(12) United States Patent
Norlien et al.

(10) Patent No.: US 10,271,788 B2
(45) Date of Patent: Apr. 30, 2019

(54) APPARATUS AND METHOD FOR MEASURING ENERGY EXPENDITURE USING INDIRECT CALORIMETRY

(71) Applicant: MGC DIAGNOSTICS CORPORATION, St. Paul, MN (US)

(72) Inventors: John A. Norlien, Pine Springs, MN (US); Daniel Stout, Little Canada, MN (US)

(73) Assignee: MGC Diagnostics Corp., St. Paul, MN (US)

( * ) Notice: Subject to any disclaimer, the term of this patent is extended or adjusted under 35 U.S.C. 154(b) by 457 days.

(21) Appl. No.: 15/054,416

(22) Filed: Feb. 26, 2016

(65) Prior Publication Data
US 2017/0245795 A1    Aug. 31, 2017

(51) Int. Cl.
| A61B 5/097 | (2006.01) |
| A61B 5/00 | (2006.01) |
| A61B 5/083 | (2006.01) |
| A61B 5/087 | (2006.01) |
| A61M 16/06 | (2006.01) |
| A61M 16/00 | (2006.01) |

(52) U.S. Cl.
CPC ............ *A61B 5/4866* (2013.01); *A61B 5/083* (2013.01); *A61B 5/0833* (2013.01); *A61B 5/0836* (2013.01); *A61B 5/0871* (2013.01); *A61B 5/097* (2013.01); *A61B 5/6803* (2013.01); *A61B 5/7275* (2013.01); *A61B 5/7278* (2013.01); *A61M 16/0069* (2014.02); *A61M 16/06* (2013.01); *A61B 2560/0204* (2013.01); *A61B 2560/0242* (2013.01); *A61B 2560/0247* (2013.01); *A61M 2230/432* (2013.01); *A61M 2230/435* (2013.01)

(58) Field of Classification Search
CPC ..................................................... A61B 5/097
USPC .................................................. 128/204.23
See application file for complete search history.

(56) References Cited

U.S. PATENT DOCUMENTS

| 4,856,531 A | * | 8/1989 | Merilainen | .......... A61B 5/0813 128/205.12 |
| 6,152,129 A | * | 11/2000 | Berthon-Jones | ............................ A61M 16/0057 128/200.24 |
| 6,884,222 B1 | * | 4/2005 | Braig | ..................... A61B 5/083 600/529 |

(Continued)

OTHER PUBLICATIONS

GlobalRPH, Determination of the Resting Metabolic Rate (RMR)—Mifflin-St Jeor equation, 2012, Web, 5 pages, Retrieved from: http://www.globalrph.com/resting_metabolic_rate.htm.*

*Primary Examiner* — Etsub D Berhanu
(74) *Attorney, Agent, or Firm* — Dewitt LLP; Thomas J. Nikolai (57) ABSTRACT

The present invention describes an apparatus and method for determining the energy expenditure of a subject by indirect calorimetry where respiratory gases $O_2$ and $CO_2$ are captured in a tent mask coupled through a pneumotach flow meter to a vacuum inlet of a blower fan whose speed is controlled by a computer running a program that ensures that the bias flow being drawn through the mask always exceeds the subject's peak expiratory flow. $VO_2$ and $VCO_2$ and flow values are measured on a breath-by-breath basis and used in arriving at a bias flow adjustment voltage to be applied to the blower fan for adjusting its speed.

9 Claims, 5 Drawing Sheets

(56) References Cited

U.S. PATENT DOCUMENTS

| | | | | |
|---|---|---|---|---|
| 2001/0004894 A1* | 6/2001 | Bourdon | ............ | A61M 16/024 |
| | | | | 128/204.23 |
| 2003/0028327 A1* | 2/2003 | Brunner | ................ | A01K 1/031 |
| | | | | 702/19 |
| 2003/0065274 A1* | 4/2003 | Mault | ................. | A61B 5/0833 |
| | | | | 600/531 |
| 2007/0274693 A1* | 11/2007 | Farbarik | ............. | A61M 16/024 |
| | | | | 388/806 |
| 2010/0275920 A1* | 11/2010 | Tham | ............... | A61M 16/0051 |
| | | | | 128/204.23 |

\* cited by examiner

APPARATUS AND METHOD FOR MEASURING ENERGY EXPENDITURE USING INDIRECT CALORIMETRY

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

I. Field of the Invention

The present invention relates generally to an apparatus and method for measuring a subject's energy expenditure, including, but not limited to, resting energy expenditure (REE), using an indirect calorimetry approach and, more particularly, to a computerized bias-flow control algorithm for insuring that a subject's entire expiration will be captured even though a face tent open collection method is being employed during the testing.

II. Discussion of the Prior Art

Measurement of energy expenditure in humans is required to assess a patient's metabolic needs, fuel utilization, and the relative thermic effect of different food, drink, drug and emotional components. Energy expenditures can be measured using one of three methods. In direct calorimetry, the rate of heat loss from the patient to the calorimeter is measured. In indirect calorimetry, oxygen consumption and/or carbon dioxide production is measured and converted to energy expenditure using an experimentally-derived formulae. A number of non-calorimetric techniques have also been used in an attempt to predict energy expenditure through extrapolation from physiological measurements and observations. Because direct calorimetry approaches tend to be very expensive to build and run. Also, they require highly experienced technicians and tend to be limited to use in highly specialized laboratories. Accordingly, indirect calorimetry is the preferred approach for measurement of energy expenditure.

Several approaches are known in the art for carrying out indirect calorimetry on a subject. In a total collection approach, a canopy or bubble-like apparatus is used to cover the upper body of a subject while in a supine position. The bubble or canopy acts as a mixing chamber for expired gasses and has a constant flow inlet. The magnitude of the inlet flow is adjusted by the operator so as to achieve a constant percentage of $CO_2$ at steady state, typically about 1%. This adjustment must be made slowly and carefully in that it is easy to overcorrect for percent $CO_2$, that is too high or too low. If the patient is left unattended and bias flow is interrupted, the patient could suffocate. While this is somewhat unlikely, it is possible. Another drawback of this method is that the patient is breathing an elevated $CO_2$ level and a depressed oxygen level. While operating at 1% $CO_2$, the effect is small but is difficult to quantify. A further disadvantage of using the rigid total collection system centers on the time required to reach a steady state equilibrium. Furthermore, significant operator skill is required to correctly adjust a bias flow.

Several years ago, applicant's assignee introduced a breath-by-breath metabolic analyzer sold under the trademark CCM Express® that would capture a patient's breath in front of his or her face and measure $CO_2$ production and $O_2$ uptake as a cross product integration of the flow and the measured percentages of $CO_2$ and $O_2$. Bias flow was achieved by a battery-powered fan with an operator adjusted potentiometer to control the speed of the fan.

In a breath-by-breath mode of collecting and measuring $O_2$ uptake and $CO_2$ production, the room air is measured before initiation of the test. The difference between this reading and the instantaneous reading obtained during the test is multiplied by the flow at the times of the particular breaths and divided by an update rate to give a volume of $O_2$ or $CO_2$ for that particular time slice. These volumes are summed over the breath and divided by the time for that breath. The end of breath is determined by noting a plateau in the $CO_2$ concentration that would correlate with the subject's inhalation. The volumes are further corrected to be reported as Standard Temperature and Pressure, Dry (STPD).

In a time-based calculation, the only difference from the breath-by-breath mode is that the time for the breath is a fixed value rather than a measured value. End of breath measurement is replaced with a fixed time marker. The length of time for the integration of the breath is determined by the operator prior to the start of the test.

The present invention overcomes many of the drawbacks of the prior art, especially the difficulty of being able to correctly adjust bias flow. In accordance with the present invention, rather than having an operator manipulate a potentiometer in order to adjust the speed of the fan causing the bias flow, the fan speed is software controlled. More particularly, the software algorithm employed automatically adjusts the bias flow to match the test conditions.

SUMMARY OF THE INVENTION

The present invention concerns a method for performing indirect calorimetry on a subject who is made to wear a tent mask coupled by a length of flexible tubing to a pneumotach flow meter whose output is coupled to a vacuum inlet of an electric motor driven blower fan whose speed is electronically controlled by a programmed computer. An oxygen, carbon dioxide and flow measurement system, also in communication with the computer, is arranged such that changes in the patient's peak respiratory flow are detected and the fan speed is adjusted on a real-time basis so that the air flow drawn through the tent mask always exceeds the patient's expiratory flow. In this way all patient exhaled carbon dioxide is captured ensuring that a computed value of resting energy expenditure is accurate.

DESCRIPTION OF THE DRAWINGS

The foregoing features, objects and advantages of the invention will become apparent to those skilled in the art from the following detailed description of a preferred embodiment, especially in conjunction with the accompanying drawings in which.

DESCRIPTION OF THE PREFERRED EMBODIMENTS

Figure 1:
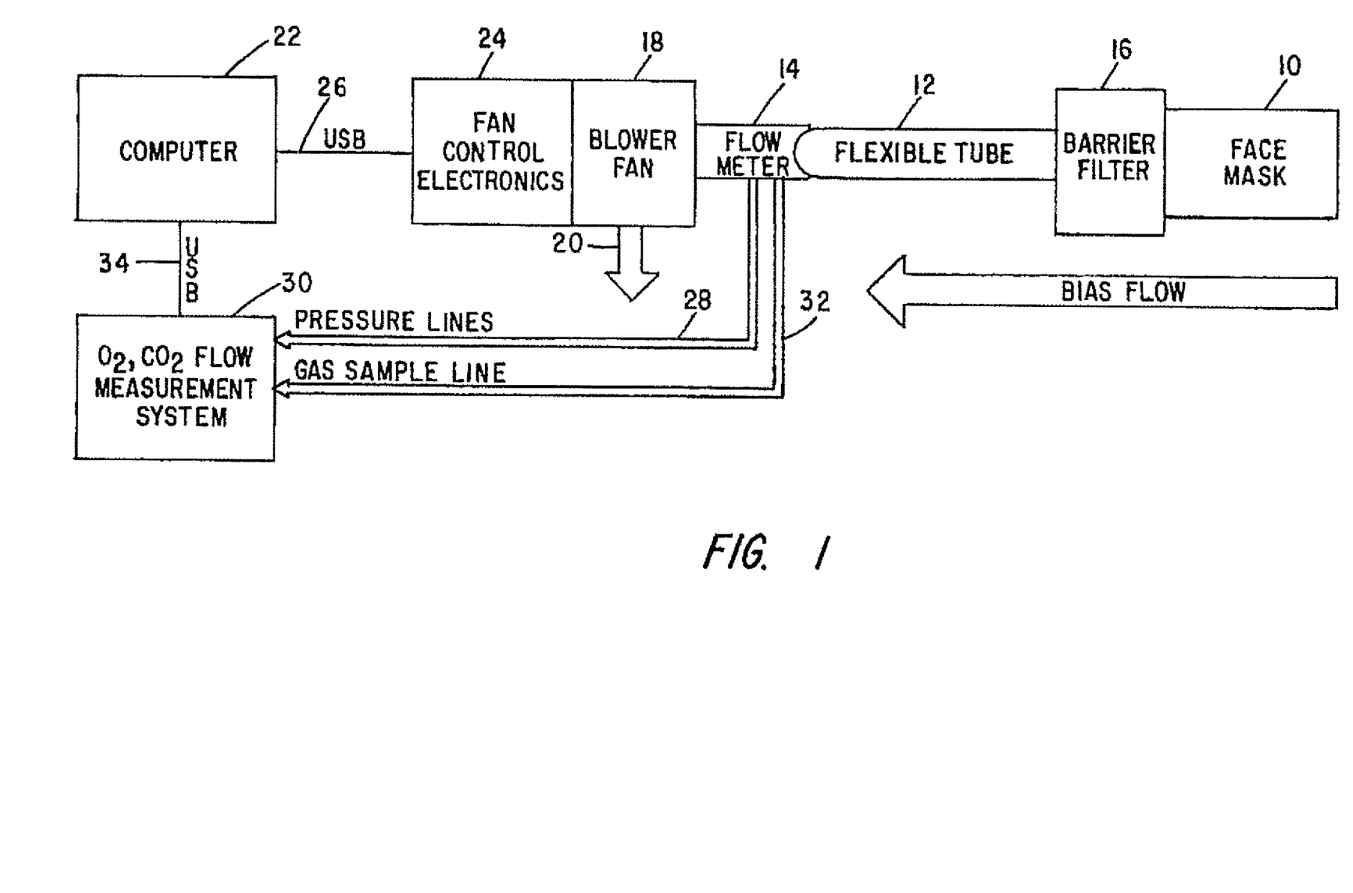
FIG. 1 is a hardware block diagram of the apparatus implementing the present invention.

Referring first to FIG. 1, there is illustrating by means of a block diagram the hardware setup for practicing the present invention. It includes a face mask 10, preferably of the tent type, which is supported by suitable straps to be located in front of a patient's mouth and nose, but is otherwise open to the atmosphere. The face mask is connected by a length of flexible hosing 12 to the input of a pneumotach flow meter 14. A barrier filter 16 is interposed between the mask and the tubing to prevent the contamination of the downstream apparatus by airborne pathogens that may be exhaled by the patient.

The flow meter 14 is preferably of the type described in the Norlien et al U.S. Pat. No. 5,038,773 that is assigned to applicants' assignee. It comprises a respiratory gas flow measuring and indicating system that incorporates a tubular, molded plastic, open-ended structure having in its lumen a pair of molded ribs which intersect to form a cross. The ribs are also tubular and each includes a series of minute apertures on opposed sides thereof which act as pitot tubes. That flow meter is more particularly described in the aforereferenced U.S. Pat. No. 5,038,773 whose contents are hereby incorporated by reference.

The output end of the flow meter 14 is connected to the vacuum inlet of a blower fan 18 and the ambient air and respiratory gases drawn by the fan are exhausted at the outlet represented by the arrow 20. The speed of the blower fan 18 is electronically controlled by a computer 22 and circuitry included in the fan control electronics module 24, the two being connected by a USB cable 26. Without limitation, the fan employed may be a series U51DL-012KK-4 miniature radial blower available from Micronel AG of Tagelswangen, Switzerland. It is a compact blower with an efficient, brushless 3-phase motor that runs very quietly with integrated driver electronics. The speed of the motor is a function of an input control voltage.

Figure 2:
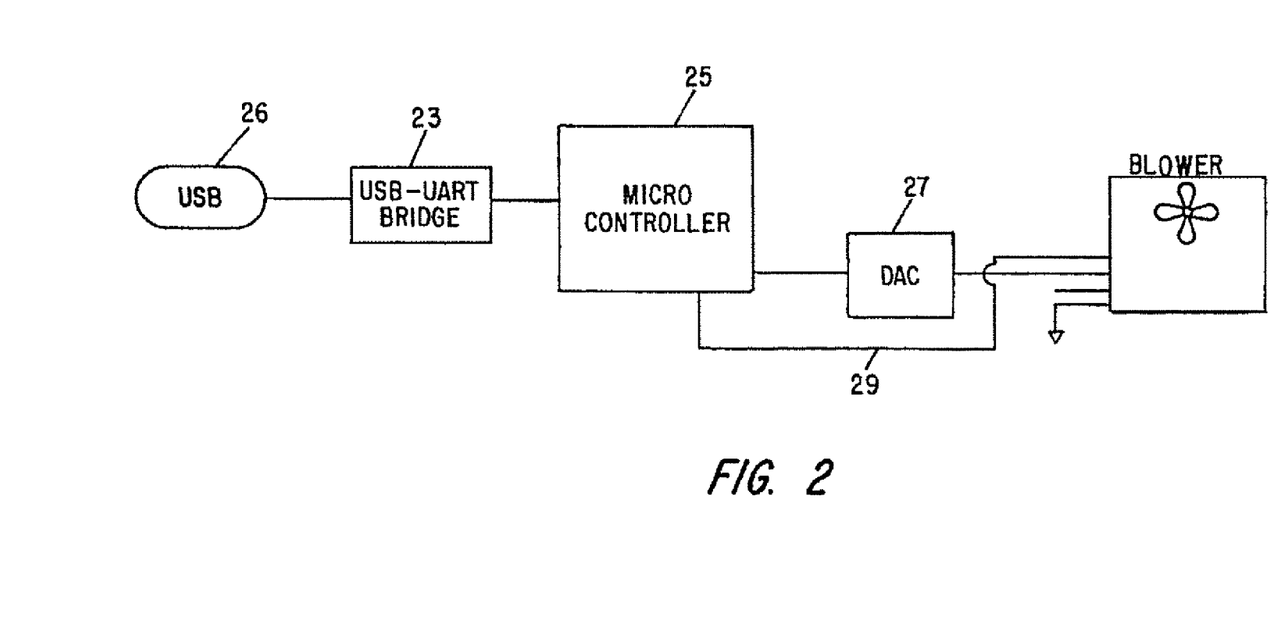
FIG. 2 is a block diagram of the fan control electronics block shown in FIG. 1.

A schematic block diagram of the fan control electronics module 24 is shown in FIG. 2. The USB cable 26 connects the computer 22 through a USB-to-UART bridge circuit 23 to a microcontroller 25 and, preferably, a MC950GAW60 available from Freescale Serviceconductor Inc. of Austin, Tex. The USB-to-UART bridge is supplied by Silicon Laboratories, Inc., also located in Austin, Tex. A digital to analog converter 27 supplies a DC voltage to the speed control input of the blower 18 and a fan speed signal is sent back from a tachometer in the blower to the microcontroller 25 via line 29.

As is explained in the afore referenced Norlien '773 patent, the pressure drop across the cruciform ribs of the flow meter 14 is proportional to the rate of flow of gas through the flow meter and the pressure lines 28 feed into the $O_2$, $CO_2$, flow measurement system 30. Likewise, samples of the gas flowing through the flow meter 14 are brought by side stream gas sample lines 32 to the measurement system 30 with a sample pump (not shown) drawing off a sample for analysis. It is also possible to measure gas concentration directly on the airstream. Flow information is derived, as explained in the Norlien '773 patent and need not be repeated here. $CO_2$ concentration is measured using known NDIR $CO_2$ sensor technology. Oxygen sensors for medical application are also commercially available. Without limitation, a type UFO-130-2 micro-fuel cell oxygen sensor available from Teledyne Analytical Instruments may be used. The measurement system 30 is also under computer control via USB cable 34. Wireless communication between the computer 22 and the modules 24 and may replace the cables with Bluetooth Global Wireless (radio wave) technology being an option.

In order to make accurate measurements of human respiration with an open system, which is afforded by the use of a face tent, the bias flow drawn by the blower fan 18 must be sufficiently high to capture the entire expiration of the patient. To achieve this, the biased flow must be greater than the patient's peak expiratory flow. If the bias flow is inadequate, expiration will spill out of the face tent such that the measured values for $VCO_2$ and $VO_2$ will be lower than the actual value.

If it is assumed that the respiratory pattern is primarily sinusoidal, it is possible to make an estimation of an adequate bias flow in terms of liters per minute. Mathematically, this assumption looks like:

Flow=$A$*sin($2\pi ft$) where $A$ is the peak flow.

By integrating over one-half period, one gets

Volume=$2*A/2\pi f$.

Since frequency, f=1/period, A=$\pi$V/period.

Since V/period is minute ventilation, with V being measured in liters and the period in minutes, to the degree that respiration can be primarily described as sinusoidal in nature:

Peak flow=$\pi$*minute ventilation.

When it is recognized that if face mask 10 comprises a face tent, minute ventilation V is not a measured parameter. However, $VCO_2$ is available as a proxy. For human respiration, measuring $VCO_2$ in ml/minute at STPD and VE in L/min at BTPS, the ratio, with a subject at rest, is in the range of 25-35. If one changes the units to both be at STPD and L/min, the ratio becomes 0.032 to 0.044. Therefore, to estimate peak flow, one should choose the smaller value of 0.032 which results in a larger estimate of peak flow.

Peak flow≈$\pi VCO_2/0.032$ or peak flow~99*$VCO_2$. This says that one must have a bias flow of about 100 times $VCO_2$ as a minimum. Taking into account the fact that expiration at the mouth is about 1.25 times as much as it would be measured at STPD, in that it is warm and saturated, the ratio for bias flow is approximately 125 times $VCO_2$, as a minimum.

Defining "dilution" as the ratio of $VCO_2$/bias flow, expressed as a percentage, it can be measured on a breath-by-breath basis during a test. If the target minimum bias flow is set at 125 times $VCO_2$, it places the maximum dilution at 0.008 or 0.8 percent. In practice, a test needs to have a consistently higher bias flow than the peak flow. It has been found in practice to be a target of 0.5%. An acceptable range would then be 0.3% to 0.7%.

It can be seen then that the bias flow needs to be greater than the minimum or else the measured values will be too small, resulting in the bias flow being adjusted to a value that is even lower. In the control methodology of the present invention, the bias flow needs to start at a rate that is higher than the target and then needs to be adjusted down to the target as the patient becomes less agitated from the strangeness of the testing procedure and settles down to a stability status. This can be done by taking a starting value for the flow based on three times the predicted $VCO_2$. Adjustment is made based on an averaged $VCO_2$ to reduce the effects of breath-to-breath variability of the measurement. The amount of adjustment is limited to a percent of value to reduce the probability of over adjustment. In practice, it has been found that limiting the adjustment to a change of no more than 10% of value works well.

The software employed, which is described in greater detail below, also allows the operator to select a time-based update of the bias flow rather than on a breath-by-breath basis. This is preferably used on patients with a higher respiratory rate, such as a pediatric patient. The reason that breath-by-breath mode does not work well is that the detection of end-of-breath requires the detection of a plateau in $O_2$ and $CO_2$ representing the inhalation phase of the respiration cycle. These plateaus tend to be filtered out by drawing the gas through the long hose 12 to the fan 18. The measurement, however, is still valid using a time-based update, as long as the dilution stays in the range described above so that the bias flow remains higher than the peak expiratory flow. As explained below, the software developed also has a manual mode where an operator can select the desired bias flow. This is useful in doing non-physiologic quality assurance tests.

Next to be described is the determination of $VCO_2$ and $VO_2$ with a subject wearing a face tent-type mask.

As a first step, one measures the ambient air and defines the fraction of inspired $O_2$ ($FIO_2$) as the measured fraction of oxygen in room air. Similarly, $FICO_2$ may be defined as the measured fraction of $CO_2$ in the room air.

Assuming that the bias flow is set appropriately so that all of the patient's expiration is captured within the bias flow, what we are measuring is the oxygen that is "missing" from the bias flow due to inhalation and the "extra" $CO_2$ present in the bias flow due to exhalation. If we define $FO_2(t)$ as the fraction of oxygen present in the bias flow at time (t) and $FCO_2(t)$ as the fraction of $CO_2$ present in the bias flow at time (t) and further define the bias flow at time (t) as Flow (t), the flow of "missing" oxygen at time (t) is then:

$$O_2\ Flow(t)=Flow(t)*(FIO_2)-FO_2(t).$$

If the update rate is set at 100 samples per second, then the time slice is 1/100 seconds, or 0.01 seconds. We multiply the flow rate $O_2$ flow(t) by this time slice to get a volume of measured oxygen during that time slice. These volumes are summed for an entire breath, or for a sufficient period of time, such that when divided by the total time of measurement, one gets the rate at which oxygen is being taken up by the patient, i.e., $VO_2$.

Similar calculations can be made with respect to $CO_2$.

$$CO_2\ Flow(t)=Flow(t)*FCO_2(t)-FICO_2(t).$$

This computed value is multiplied by the time slice and summed up for the entire breath. The result is then divided by the time for the breath yielding $VCO_2$. Finally, by dividing the computed values of $vO_2$ by $VCO_2$, we obtain the resting energy expenditure, REE.

Having described the system apparatus and the underlying theory of operation, attention will next be given to the software algorithms executed by the computer 22 for periodically adjusting the bias flow drawn through the tent mask 10 to insure that the patient's peak expiratory flow is captured and drawn through the hose 12 and the flow meter 14 so that the concentration of $O_2$ and $CO_2$ can be accurately measured and REE computed.

Figure 3A:
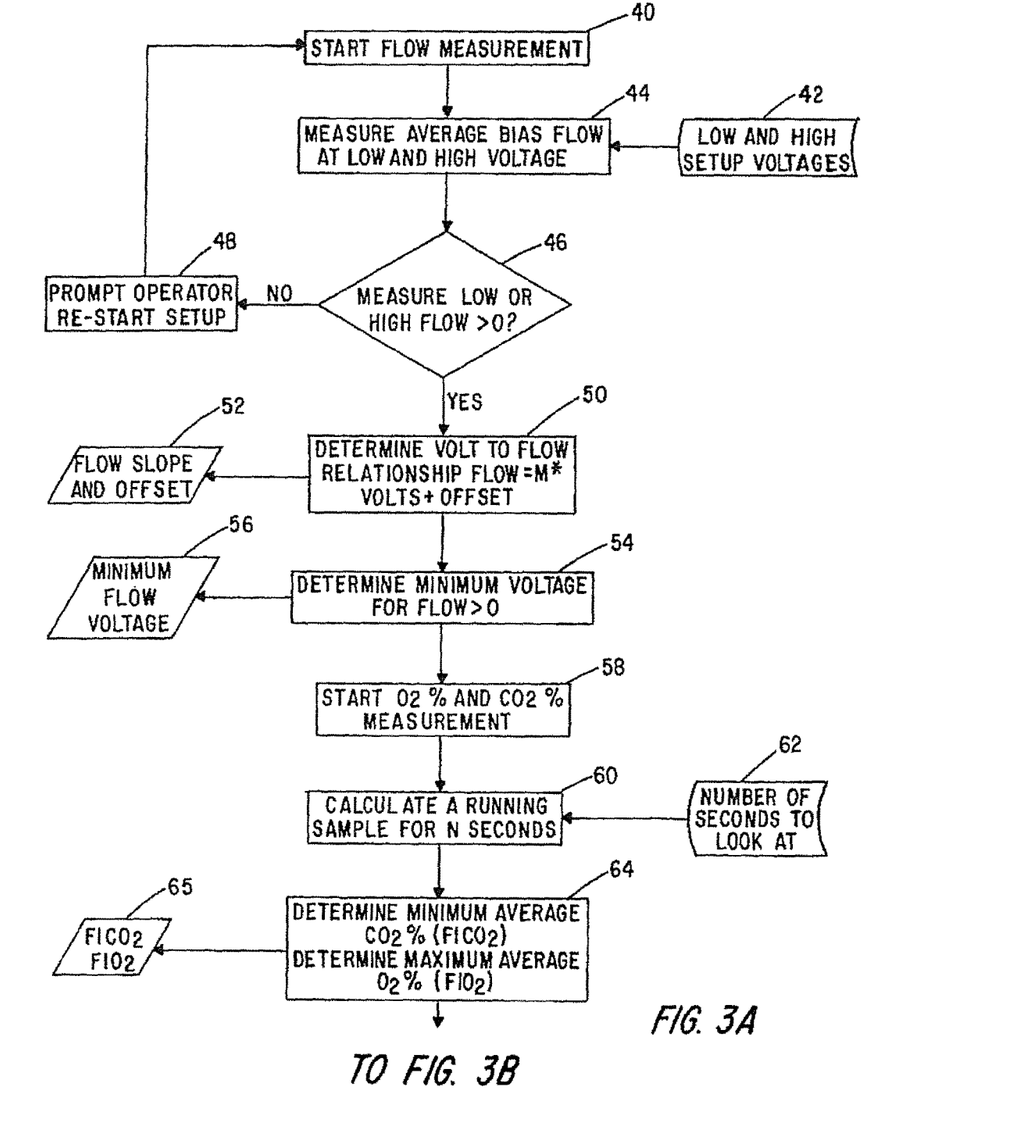
FIG. 3A is a flow chart illustrating the steps comprising the test setup procedure.

FIG. 3A is a software flow chart of the steps involved in setting up the equipment preparatory to administering a test on a subject. The first step, represented by block 40, is to begin measuring the bias flow and, more particularly, as reflected by blocks 42 and 44 perform flow measurements at low and high fan speeds corresponding to preset low and high setup voltages.

To check whether the bias flow system is working properly, a test is made at decision block 46 to determine whether the low or high flow is more than a no flow condition. If not, the operator is prompted to check out the hardware setup and restart operations (block 48).

If the test at decision block 46 indicates the presence of bias flow, an operation is performed at block 50. However, if the test at block 46 shows that the flow varies with an input voltage change, the next step is to determine a voltage-to-flow relationship using the liner equation y=mx+b. In the context of the present invention, the equation is:

$$Flow=m*volts+offset$$

In carrying out the step of block 58:
Let $V_L$=low voltage used and $V_H$=high voltage used.
Let $F_L$=flow observed with low voltage and $F_H$=flow observed with high voltage used. Then:

$$Slope=(F_H-F_L)(V_H-V_L),\ intercept=F_L-slope*V_L$$

Following this computation, flow slope and offset are stored for subsequent use (block 52).

The next operation performed is to determine the minimum voltage for a flow greater than 0 and to store this value (blocks 54 and 56). While the relationship between measured flow and voltage applied to the blower is quite linear, there is a voltage that must be exceeded before the blower rotor will move to produce a flow greater than 0. This provides a voltage value that constitutes a lower limit in that below this value, no air is being drawn from the patient for measurement and the test fails.

Next, and as indicated by block 58, measurements of percentage concentrations of $O_2$ and $CO_2$ in the ambient room air takes place. The measurement is taken over a predetermined period of time, measured in seconds, to obtain a running sample over a preset time interval (blocks 60 and 62). Having obtained the samples, next the minimum average $CO_2$ percentage and the maximum average $O_2$ percentage are computed so that the ambient room values are established and these values are stored for later use (blocks 64 and 65). Those skilled in the art will recognize that even if a subject is breathing on the system so that it is already capturing some of what the subject is exhaling, by getting the minimum $CO_2$ and the maximum $O_2$ during that time interval, it is the ambient values that are captured and these values are stored for later use.

Figure 3B:
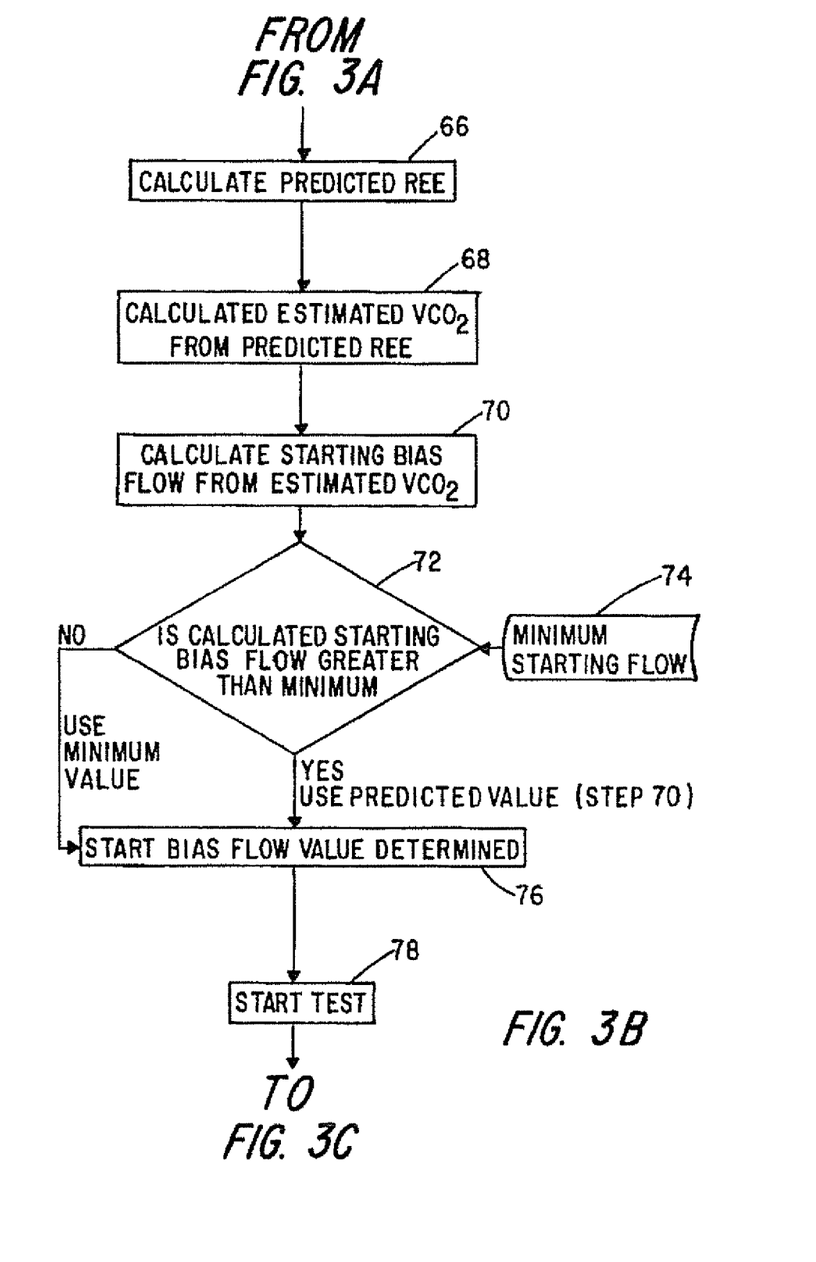
FIG. 3B is a software flow chart of the steps for arriving at a starting bias flow value.

The next steps in preparing for actually running a test on the patient is to calculate a starting bias flow to be used. These steps are shown on the software flow diagram of FIG. 3B which begins with calculating a predicted resting energy expenditure (REE) representing the amount of calories required for a 24-hour period by the body during a non-active period. Energy expenditure can be estimated or predicted using various known and published formulae which take into account a subject's race, age, weight, body mass index, gender, height, etc. The Harris-Benedict prediction equation is one such formula. Another is the abbreviated Weir equation:

$$REE=[3.9(VO_2)+1.1(VCO_2)]1.44$$

where $VO_2$ is oxygen uptake in ml/min and $VCO_2$ is carbon dioxide output in ml/min. The so-called respiratory quotient $(RQ)=VCO_2/VO_2$. This step is represented by block 66 on FIG. 3B.

Once a Predicted REE is established, an estimated $VCO_2$ can be derived based upon the calculated "Predicted REE" from step 66. Using the Weir formula and the assumed RQ value of 0.8, estimated $VO_2$ is equal to "Predicted REE" divided by 6.95.

Knowing the estimated $VCO_2$ from step 68, an estimated starting bias flow can be arrived at. With respect to step 70, in that dilution is defined as $VCO_2$/bias flow where both are measured in liters per minute, and if a target dilution of 0.5% is desired, then "bias flow target" would be $$\frac{1}{.005} * VCO_2$$

or 200*$VCO_2$.

Next, a test is made at decision block 72 of whether the calculated starting bias flow resulting from step 70 is greater than a pre-established minimum starting flow that had earlier been established based on earlier testing (block 74). A voltage is applied to the blower to establish a starting bias flow based on the predicted calculated value. If it is less, the minimum starting flow value from block 74 is used instead.

Experience has shown that the starting bias flow needs to initially be higher because when patient's begin the test, their $VCO_2$ is at a higher value. During the test it drops as the patient settles in and any nervousness or agitation due to surrounding activity decreases. It has been found that a good starting place is approximately 3 times the estimated steady state flow.

At block 76, a voltage corresponding to the start bias voltage is applied to the blower and the test may be started where patient measurements are taken and the bias flow is adjusted under computer control to always ensure that the bias flow is sufficient to capture all $CO_2$ being exhaled into the bias flow stream. The patient-testing phase is set out in the software flow diagram of FIG. 3C.

Figure 3C:
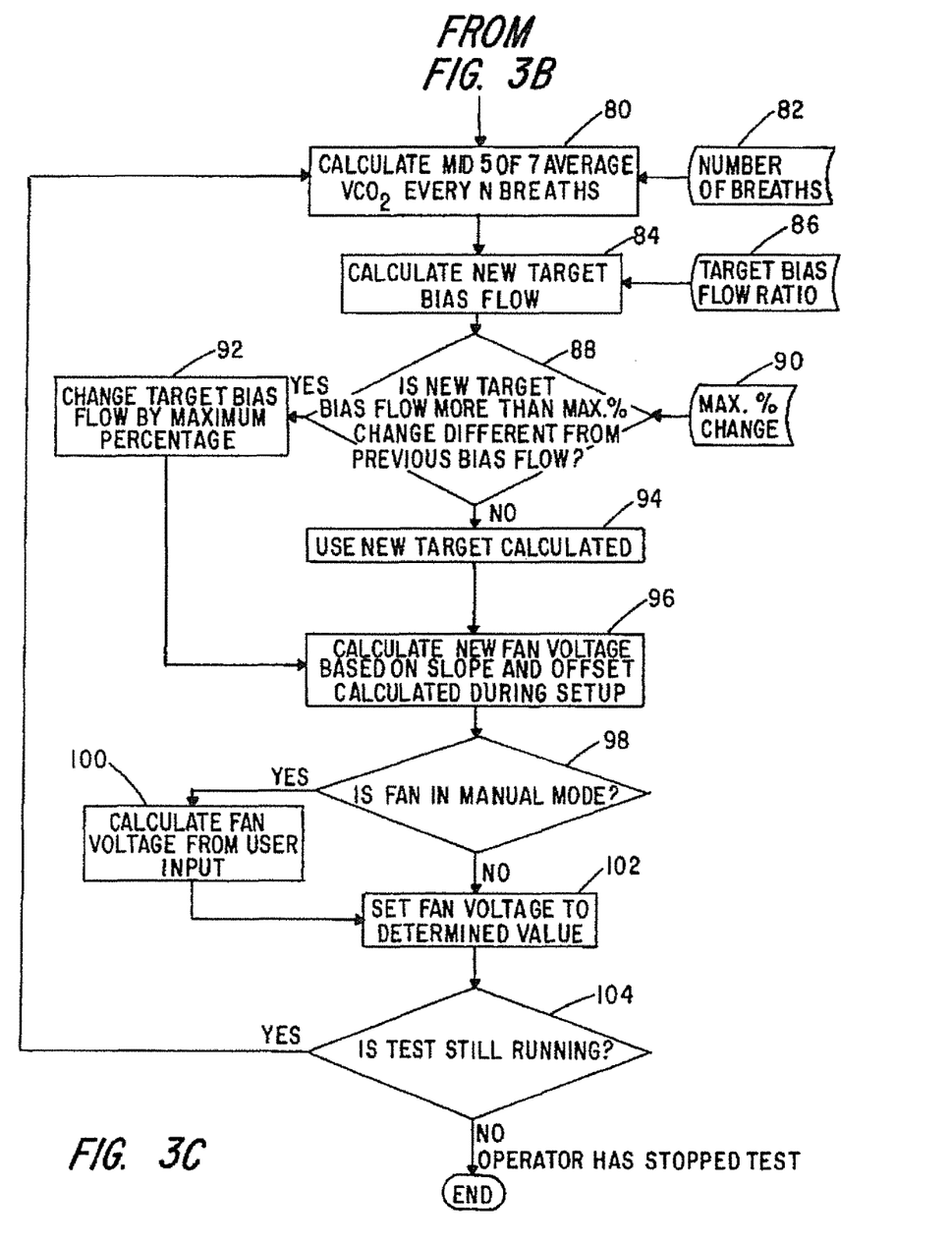
FIG. 3C is a software flow diagram of the steps involved in accumulating patient data.

FIG. 3C illustrates the steps taking place during testing of a patient. At block 80 on FIG. 3C, a calculation is made of the volume of carbon dioxide that the patient breaths out during a predetermined number of breaths, e.g., 7 breaths, and it is averaged over a lesser number of breaths, e.g., 5 breaths, by means of the equation:

$VCO_2$ (ml/min)=VE*(FeCO$_2$–FiCO$_2$)

where VE stands for the volume of air expired in ml/min. The number of breaths used in the calculation is a programmable quantity entered from a storage register in the computer and is represented by block 82 in FIG. 3C. By making the above calculation based on a predetermined number of breaths, changes of fan speed on every breath are avoided so that from the patient's perspective he or she is only hearing the fan speed change every several breaths, which typically avoids changes in fan speed taking place more than about every 40 seconds. Also, filtering occurs to eliminate coughing episodes and momentary spikes. By collecting 7 breaths, and throwing out a high and a low and then averaging the middle 5 breaths, anomalies due to coughing or swallowing are eliminated.

At block 84, a new target bias flow is calculated based on the $VCO_2$ value arrived at during step 80. It will be recalled that the new target bias flow is equal to 200*$VCO_2$ for a target dilution of 0.5%. The target bias flow ratio from block 86 is the ratio of average $VCO_2$ divided by the average flow.

Once a new target bias flow has been arrived at, a test is made at decision block 88 as to whether the new target bias flow is more than a maximum percent change from a previous bias flow. The maximum percentage change is a variable that can be set by the operator. The change allowed in bias flow is limited in this manner to reduce the probability of over-correction that can result in oscillation. A limit of 10% change has been found to be a good default value. If the new target flow calculated in step 84 is more than, say 10%, the target bias flow is only changed by the maximum percentage change value selected. See block 92. However, if the new bias flow is equal to or less than the maximum percentage change allowed, the new target bias flow calculated in step 84 is used (block 94).

Again, assuming that the new target bias flow has exceeded the maximum percentage change value and that the target bias flow has been changed by the maximum percentage, a new fan voltage is calculated based on the slope and offset calculated during setup. See block 58 on FIG. 3A. This operation is represented by block 96 in FIG. 3C.

As indicated earlier, the software also permits operation in a manual mode. This allows an operator to set the blower speed by setting in an operator-selected bias flow value. Hence, in FIG. 3C, block 98 represents a check that is made to see if the operator has selected the manual mode. If so, at step 100, a fan voltage is calculated based upon the selected bias flow value. As represented by block 102, the fan voltage is set either to the one based on the user input or the one based on the value arrived at in step 96.

Lastly, a test is made at decision block 104 to sense whether the test continues to run. If it does, control loops back to block 80 and the test cycle is repeated.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices. Also, various modifications, both as to the equipment and operating procedures, can be accomplished without departing from the scope of the invention itself.

What is claimed is:

1. A method for adjusting bias air flow into a tent mask worn by a patient during an indirect calorimetry assessment on the patient comprising the steps of:
    (a) placing a tent mask on the patient's face where the tent mask is coupled by flexible tubing to an input of a pneumotach flow meter having an output coupled to a vacuum inlet of an electric motor-driven blower fan whose speed varies with applied blower fan voltage and is electronically controlled;
    (b) providing an oxygen, a carbon dioxide and a flow measurement system coupled to the pneumotach flow meter, said oxygen, carbon dioxide and flow measurement system providing measured oxygen and carbon dioxide concentrations within the tent mask;
    (c) providing a computer coupled in controlling relation to the blower fan motor and also coupled to receive the measured oxygen and carbon dioxide concentrations from the oxygen, carbon dioxide and flow measurement system; and
    (d) executing a program on the computer for adjusting the blower fan voltage based on the measured carbon dioxide concentration in an air flow being drawn through the tent mask to ensure that the airflow always exceeds the patient's peak expiratory flow with dilution less than a predetermined target value.

2. The method as in claim 1 wherein the program first causes the oxygen, the carbon dioxide and flow measurement system to measure the concentration of oxygen and carbon dioxide in samples of room air over a predetermined time period and to calculate a minimum average percentage concentration of carbon dioxide and a maximum average percentage of oxygen in said samples.

3. The method as in claim 2 wherein the time period is a programmable parameter.

4. The method as in claim 1 wherein the program determines a relationship between voltages applied to the blower fan motor and a resulting bias flow being drawn by the blower fan.

5. The method as in claim 4 and further including a step where a minimum voltage to produce the bias flow is determined.

6. The method as in claim 4 and further including the step of calculating a predicted resting energy expenditure based upon the patient's demographic parameters and determining from said resting energy expenditure one of an estimated volume of carbon dioxide per minute expired by the patient and an estimated volume of oxygen per minute being utilized by the patient.

7. The method as in claim 6 where the program further includes a step of calculating from one of a plurality of known estimation formulas based on the patient's height, weight and age a volume of carbon dioxide per minute expired by the patient and a volume of oxygen per minute utilized by the patient as a starting bias flow to be drawn through the tent mask by the blower fan.

8. The method as in claim 1 wherein the program calculates an average of a volume of carbon dioxide per minute exhaled by the patient over a predetermined number of breaths and based thereon determines a new target bias flow and then tests whether the new target bias flow results in a change from a previous target bias flow that exceeds a predetermined limit.

9. The method as in claim 8 and further including a step of calculating a new fan voltage for the blower fan motor based upon the new target bias flow and applying that new fan voltage to the motor for the blower fan.

* * * * *